United States Patent [19]
Lin

[11] Patent Number: 5,910,119
[45] Date of Patent: Jun. 8, 1999

[54] ULTRASONIC COLOR DOPPLER VELOCITY AND DIRECTION IMAGING

[75] Inventor: Gregory Sharat Lin, Fremont, Calif.

[73] Assignee: Diasonics, Inc., Milpitas, Calif.

[21] Appl. No.: 09/076,669

[22] Filed: May 12, 1998

[51] Int. Cl.[6] .................................................. A61B 08/00
[52] U.S. Cl. ........................... 600/455; 600/437; 600/454
[58] Field of Search .................................... 600/455, 443, 600/437, 453, 459, 454; 178/916

[56] References Cited

U.S. PATENT DOCUMENTS

| | | | |
|---|---|---|---|
| 5,375,600 | 12/1994 | Melton, Jr. et al. | 600/455 |
| 5,409,010 | 4/1995 | Beach et al. | 600/455 |

Primary Examiner—William E. Kamm
Assistant Examiner—Maulin Patel
Attorney, Agent, or Firm—Blakely, Sokoloff, Taylor & Zafman

[57] ABSTRACT

A system is disclosed for performing ultrasonic color Doppler imaging to produce absolute velocity and flow direction information for complex media. Ultrasonic color Doppler beams are steered at two different angles and samples are taken at the points of intersection between the steered beams. The duplex color Doppler sample volumes are two overlapping sample volumes interrogated from different angles. Frequency-shift information provided by the color Doppler sample volumes are used to compute the absolute mean velocity and direction of motion of acoustic reflectors within the sample volumes. Velocity and direction data are computed for a two-dimensional array of duplex color Doppler sample volumes and mapped into a color scale to provide a spatial distribution of the velocity or direction of flow or motion of acoustic reflectors.

26 Claims, 14 Drawing Sheets

Arterial waveform

Baseline

700

$$PI = \frac{\Delta f_{max} - \Delta f_{min}}{\Delta f_{time-avrg}}$$

Venous waveform

Baseline

702

ULTRASONIC COLOR DOPPLER VELOCITY AND DIRECTION IMAGING

FIELD OF THE INVENTION

The present invention relates generally to medical devices, and more specifically to ultrasonic imaging of the absolute velocity and direction of flow in complex media.

BACKGROUND OF THE INVENTION

Ultrasonic imaging technology has become a vital tool for examining the internal structure of living organisms. For the diagnosis of various medical conditions, ultrasonic imaging is often useful to examine soft tissues within the body to show the structural detail of internal tissues and fluid flow.

To examine internal body structures, ultrasonic images are formed by producing very short pulses of ultrasound using a transducer, sending the pulses through the body, and measuring the properties (e.g., amplitude and phase) of the echoes from tissues within the body. Focused ultrasound pulses, referred to as "ultrasound beams", are targeted to specific tissue regions of interest in the body. Typically, an ultrasound beam is focused at various steps within the body to improve resolution or image quality. Echoes are received by the transducer and processed to generate an image of the tissue or object in a region of interest. The resulting image is usually referred to as a B-scan image.

Measuring and imaging blood (and other bodily fluid) flow within a living subject is typically done using the Doppler principle, in which a transmitted burst of ultrasound at a specific frequency is reflected from moving blood cells, thereby changing the frequency of the reflected ultrasound in accordance with the velocity in the direction of the flow. The frequency shift (Doppler shift) of reflected signals with respect to the transmitted signals is proportional to the velocity of the fluid flow. This frequency may be detected and displayed on a video display device to provide graphic images of moving tissue structure and fluid flow within a living patient.

Present ultrasound techniques include frequency-shift color Doppler and power color Doppler imaging of tissue motion, as well as cross-correlation ultrasound estimation of displacements and mean velocities for color mapping tissue motion (referred to as CVI and developed by Philips Corp.). These present known methods of ultrasound imaging provide relatively limited information regarding the velocity and direction of flow in complex media. For example, present color Doppler flow imaging techniques (CDI) provide only frequency-shift data that is dependent on both the velocity of fluid flow or tissue motion and the Doppler angle between the ultrasound beam and the direction of flow or motion. This method provides neither the absolute velocity of the flow or motion, nor the direction of flow or motion.

The cross-correlation technique (CVI) produces and displays a limited range of velocities of flow or motion. Although CVI systems can be calibrated to produce absolute velocities and flow direction, the algorithms involved are complex and computationally intensive, thus requiring increased processing time and computer resources. Furthermore, because the uncertainty in cross-correlation estimates of velocity and direction tend to be large, the signal-to-noise ratio of this method is likely to be poor.

SUMMARY OF THE INVENTION

A system is described for performing ultrasonic imaging of the absolute mean velocity and direction of flow or motion in complex media, including soft biological tissue. Two conventional ultrasonic color Doppler beams are steered at two different angles such that sampling is done at the point of intersection between the two differently-steered color Doppler beams. These duplex color Doppler sample volumes are two overlapping sample volumes interrogated from different angles. This type of over-sampling provides sufficient frequency-shift information from which to compute the absolute mean velocity and direction of flow or motion of acoustic reflectors. Velocity and direction data are computed for a two-dimensional array of duplex color Doppler sample volumes and mapped onto a color scale to provide a spatial distribution of the velocity or direction of flow or motion of the acoustic reflectors. The principal application of this technique is in visualizing the absolute velocity and direction of blood flow or soft tissue motion in a living body.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements, and in which.

DETAILED DESCRIPTION

A system is described for performing ultrasonic imaging of the absolute mean velocity and direction of flow or motion in complex media, including soft biological tissue. Target tissue is imaged using two ultrasonic color Doppler beams introduced at different angles such that sampling is performed at the point of intersection between the two beams. The absolute mean velocity and direction of flow or motion of acoustic reflectors within the target tissue is computed from the frequency-shift information at the sample volumes.

It is an intended advantage of embodiments of the present invention to provide a device which performs ultrasonic color Doppler imaging of the absolute velocity and direction of fluid flow or tissue motion in complex media.

It is a further intended advantage of embodiments of the present invention to provide a system that displays color differentiation between arterial and venous blood flow within a body.

Various embodiments of the present invention may be implemented in discrete hardware components or, alternatively, in programmed processing units such as digital signal processors using software which is compiled, linked and then loaded from disk-based storage for execution during run-time. Various programs containing the methods employed in these embodiments may also reside in firmware or other similar nonvolatile storage means.

Figure 1:
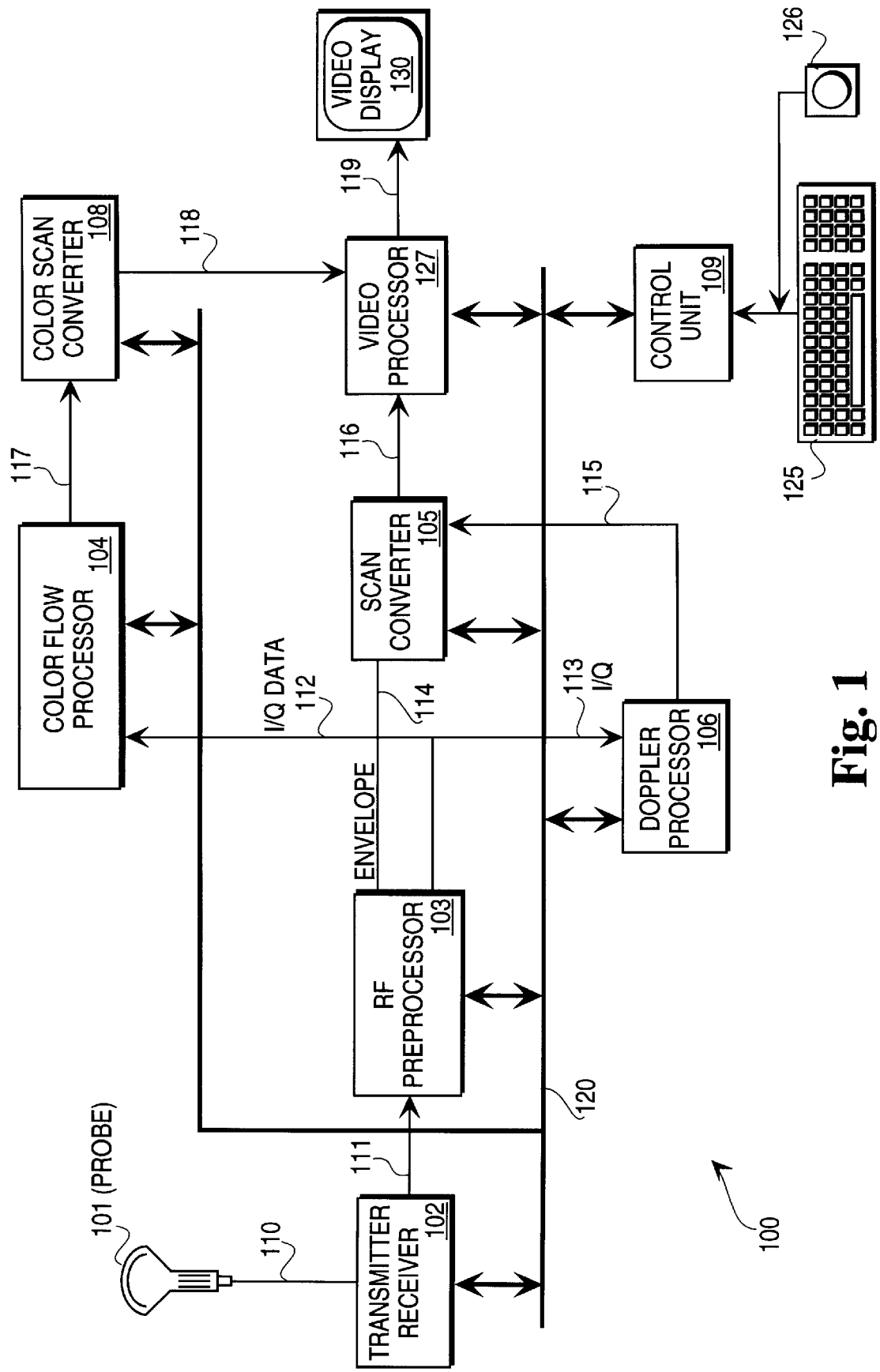
FIG. 1 is a block diagram of an ultrasonic imaging system that incorporates embodiments of the present invention.

FIG. 1 illustrates a block diagram of an ultrasonic imaging system that incorporates embodiments of the present invention. Imaging system 100 includes an ultrasonic transducer 101 (also referred to as a "probe"), which is typically a multi-element array of piezoelectric elements that both send and receive ultrasound signals when examining a subject, such as a living patient. Probe 101 is coupled through signal path 110 to transmitter/receiver circuit 102, which is designed according to principles known in the ultrasound imaging art, and which, for purposes of brevity, will not be discussed in further detail.

Transmitter/receiver circuit 102 is coupled to a control unit 109 through bus 120, and is controlled so that the elements in probe 101 are focused at particular points in the body during both transmission and reception of ultrasound signals. Transmitter/receiver circuit 102 and control unit 109 also often provide a scanning function so that a two-dimensional image may be generated without moving probe 101 with respect to the body.

Following transmission of ultrasound signals into the body, reflected signals are processed by a receiver (known as a "beamformer") in transmitter/receiver circuit 102. The multitude of signals from each individual element of probe 101 are converted into a single signal which is sent to Radio Frequency (RF) processor 103 through signal path 111. In one embodiment of the present invention, the beamformer circuit within transmitter/receiver 102 receives steered color Doppler pulses that provide sufficient frequency shift information to compute mean velocity and direction of flow of acoustic reflectors within the targeted area of the body.

RF processor 103 processes the signal information to produce a demodulated envelope signal and in-phase (I) and quadrature (Q) Doppler signals. The envelope signal represents the amplitude of echoes returning from the body and is further transmitted through signal path 114 to a scan converter 105 which is a typically implemented as a large digital electronic memory.

Scan converter 105 stores the envelope echo information on a line-by-line basis together with the geometrical position of such information in the body resulting from the scanning process, in such a manner that a two-dimensional image may be constructed and transmitted to video processor 127 through signal path 116.

In the absence of any color Doppler information, video processor 127 simply sends an image signal over signal path 119 to video display monitor 130. This two-dimensional image, usually black and white, represents the distribution of echo generating sites within the body. The so-called B-scan image is then used by the operator to search the body for pathology or is used by a physician to develop a diagnosis.

I and Q signals for spectral Doppler are sent to Doppler processor 106 through signal path 113. Doppler processor 106, under the control of control unit 109 through bus 120, compares signals from several successive received echoes to determine the Doppler shift in a single region in the body which is commonly known as the sample volume. Doppler processor 106 also produces a continuous time series of spectral Doppler information in which blood flow velocities are displayed in black and white on video display 130 over one or more cardiac cycles (typically several seconds). The Doppler information is transmitted to scan converter 105 through signal path 115, and then to video processor 127 through signal path 116 for ultimate display on video display 130.

RF processor 103 transmits I and Q signals through signal path 112 to color flow processor 104. Color flow processor 104 typically processes several sample volumes along a given scanning direction in the body: Color flow processor passes signals to color scan converter 108 through signal path 117. In color scan converter 108, color encoded signals are stored on a line-by-line basis, together with the geometrical position of such information in the body resulting from the scanning process. In this manner, a two-dimensional color video image is constructed and transmitted to video processor 127 through signal path 118.

Color scan converter 108, which may also be used to interpolate scan line information obtained from color flow processor 104, then transmits color Doppler information through signal path 118 to video processor 127 for display on video display 130. Video processor 127 typically includes decision circuits to choose whether a given specific part of the two dimensional image has color information resulting from flow or whether it only has echo information from static tissue. If flow is present, the color information is displayed at the correct point in the image rather than the black and white image information. In one embodiment of the present invention, color flow processor 104 processes instructions that allow system 100 to calculate and display velocity and direction information for tissue motion and fluid flow within the body.

Velocity and Direction Imaging

In one embodiment of the present invention, the ultrasound system of FIG. 1 incorporates a linear array ultrasound transducer and color Doppler ultrasound scanner that are capable of electronic beam steering which is used to measure the velocity and direction of acoustic reflector flow in complex media. Color Doppler beams are steered and introduced into the tissue at two equal but opposite angles. A coincident (duplex) color Doppler sample volume is located at each point of intersection between two oppositely-steered color Doppler beams. This method generates two independent frequency-shifts at the same point in the tissue.

Figure 2:
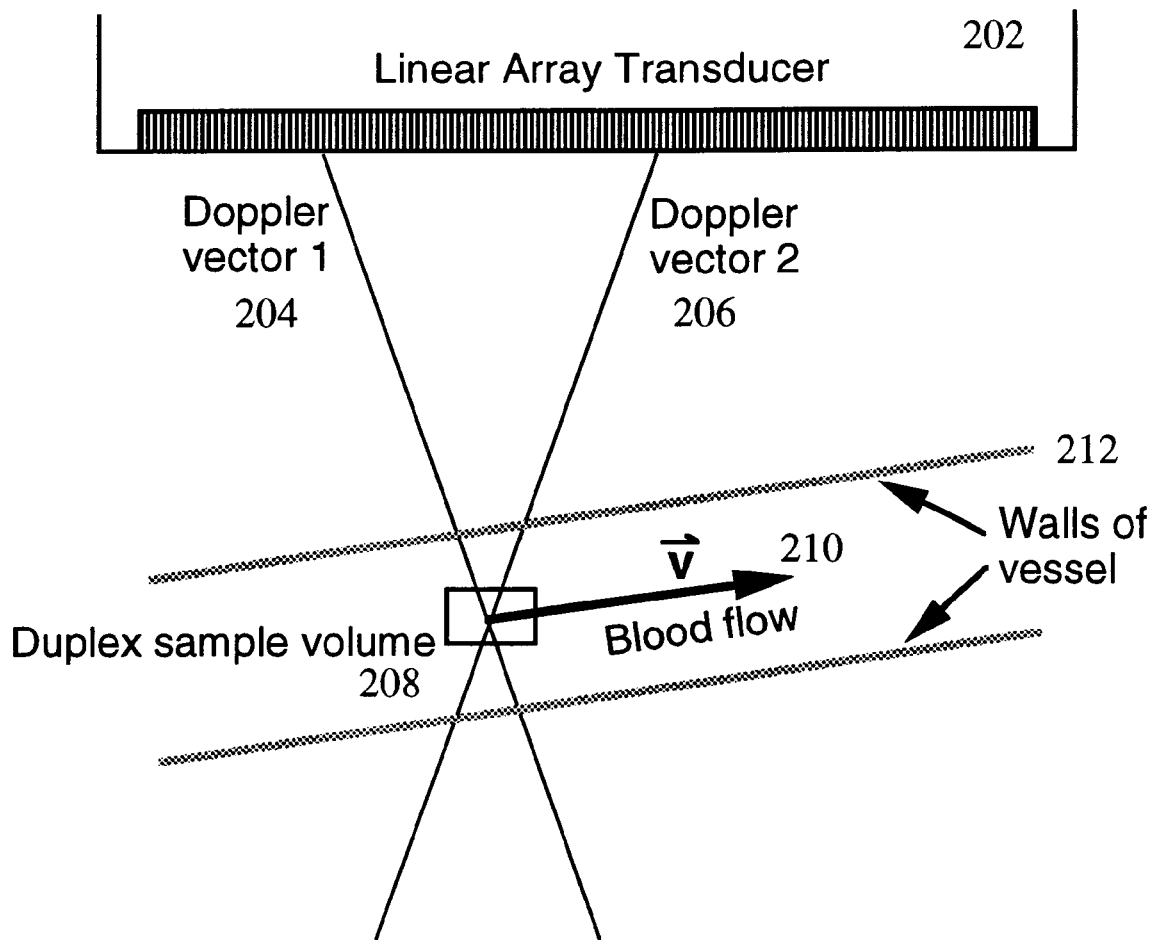
FIG. 2 illustrates a duplex color Doppler sample volume detecting fluid flow through a point in a vessel or similar tissue structure.

FIG. 2 illustrates a duplex color Doppler sample volume detecting fluid flow through a point in a vessel or similar tissue structure. Vessel 212, which typically is a blood vessel, contains the target tissue or area in a region of interest 208. A linear array transducer 202 produces two separate Doppler vectors that are incident to the target tissue area 208. The two vectors are denoted Doppler vector 1, 204, and Doppler vector 2, 206. The purpose of the two Doppler vectors 204 and 206 is to determine the absolute magnitude and direction of flow vector 210 that represents the flow of the target tissue 208.

It should be noted that the two Doppler samples taken using the two Doppler vectors must be taken very close together in time in order to provide accurate data for the moving tissue or fluid. In one embodiment of the present invention, a sequence of angle-interleaved steered color Doppler vectors is fired across the length of the color Doppler region of interest, e.g., tissue area 208 in FIG. 2. The sequence of angle-interleaved steered color Doppler vectors is produced by the linear array transducer 202. A region of interest is formed by an operator-defined subset of the area containing pixels located at intersecting vector pairs.

Figure 3:
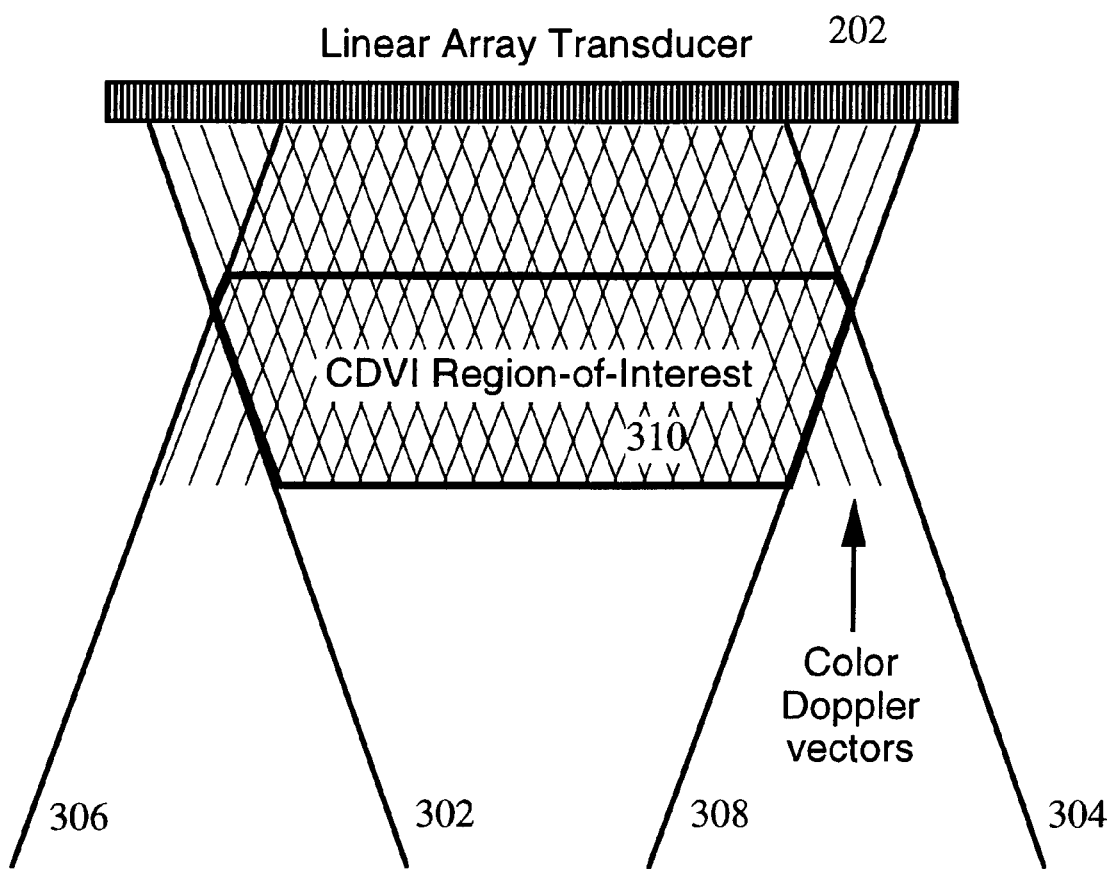
FIG. 3 illustrates the generation of a region of interest using intersecting vector pairs of angle-interleaved steered color Doppler vectors, according to one embodiment of the present invention.

FIG. 3 illustrates the generation of a region of interest using intersecting vector pairs of angle-interleaved steered color Doppler vectors, according to one embodiment of the present invention. Linear array transducer 202 generates a series of vectors at a first angle. The first vector at the first angle is shown as vector 302 and the last vector at this angle is shown as vector 304. In between these two vectors is a number of additional vectors at this same angle. Linear array transducer 202 also generates a series of vectors at a second angle. The first vector at the second angle is shown as vector 306 and the last vector at this angle is shown as vector 308. In between these two vectors is a number of additional vectors at this same angle. The intersection of the two sets of vector sequences defines a region of interest 310. Individual pixels within the region of interest are defined by the intersection of pairs of vectors, with one vector incident to the pixel at the first angle and the other vector incident to the pixel at the second angle.

Figure 4:
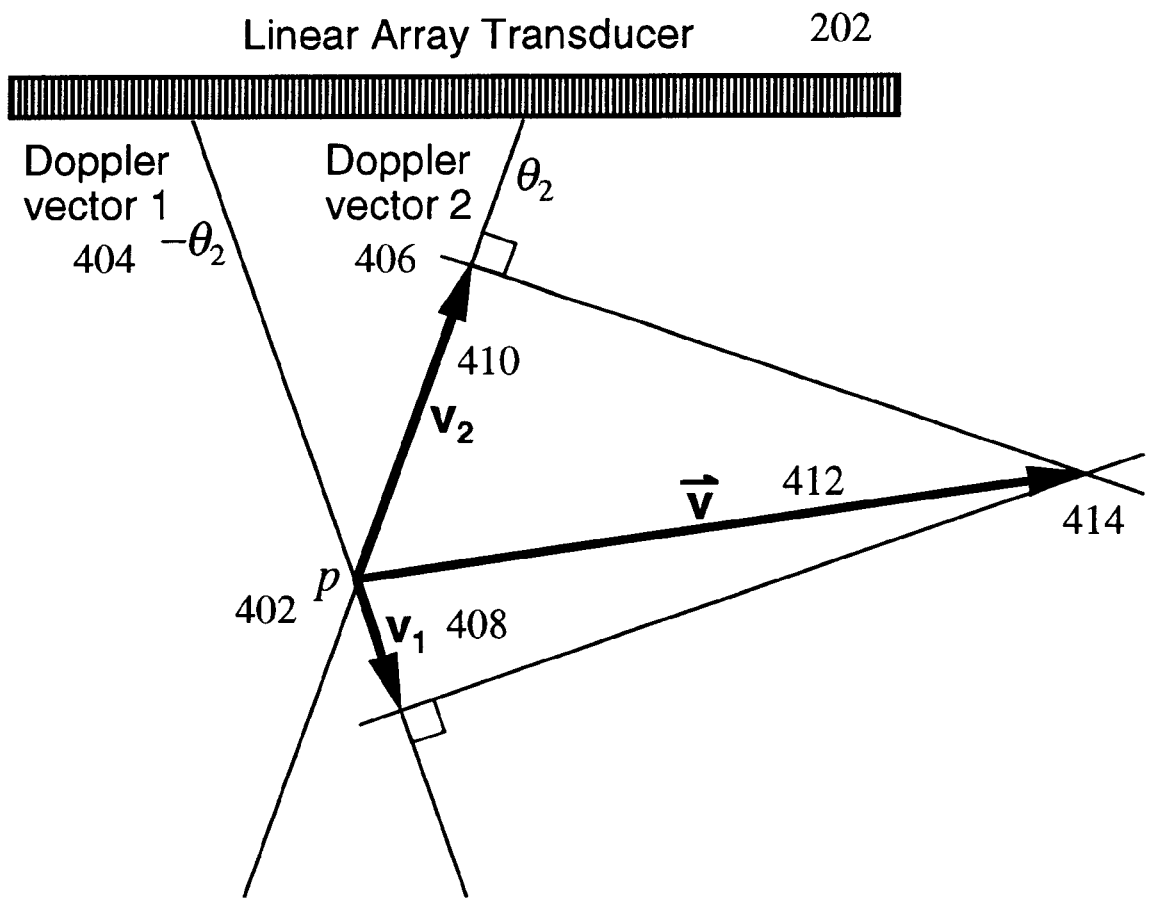
FIG. 4 illustrates the computation of the velocity vector for a pixel within a region of interest produced by intersecting vector pairs.

FIG. 4 illustrates the computation of the velocity vector for a pixel within the region of interest. Pixel p 402 represents the pixel at the intersection of two Doppler vectors, Doppler vector 1 and Doppler vector 2, generated by linear array transducer 202. The motion at pixel p is represented by velocity vector $\bar{v}$, 412. The two color Doppler vectors intersecting at pixel p each return frequency shifts proportional to the respective axial components of velocity vector $\bar{v}$ The axial component along Doppler vector 1, 404, is denoted $v_1$ 408 and the axial component along Doppler vector 2, 406, is denoted $v_2$ 410.

Figure 5:
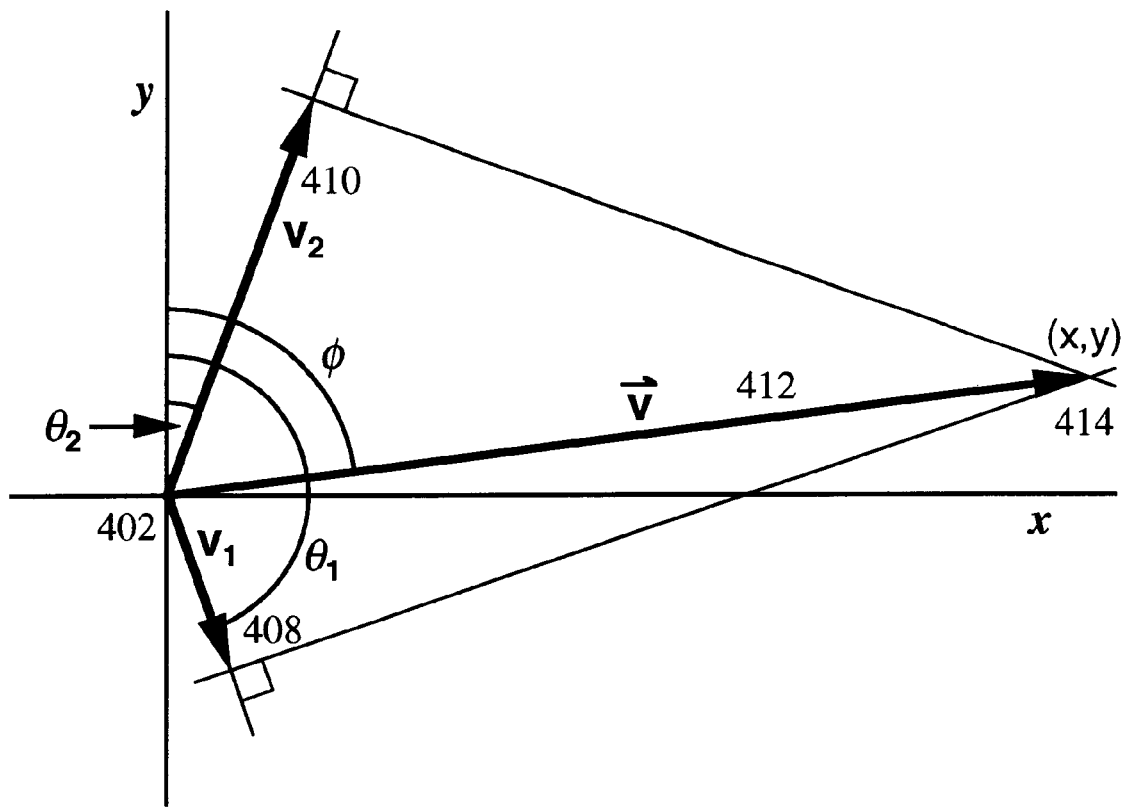
FIG. 5 illustrates the computation of the magnitude and direction of the velocity vector of FIG. 4.

The magnitude and direction of the velocity vector $\bar{v}$, 412 can be computed from the axial velocity components, $v_1$ and $v_2$ and their vector angles, $\theta_1$ and $\theta_2$, as illustrated in FIG. 5. Using a Cartesian coordinate system centered at pixel p, 402, the axial velocity components lie on the lines of the steered color Doppler vectors 408 and 410. The angular relationships of these axial velocity components is provided by the following equations:

$$\text{for } v_1\text{: } y = \tan\theta_1 \cdot x \qquad [1]$$

$$\text{for } v_2\text{: } y = \tan\theta_2 \cdot x \qquad [2]$$

When the velocity vector $\bar{v}$ 412 is projected onto each steered color Doppler vector, it is decomposed into its axial velocity components by dropping the following orthogonal lines to each color Doppler vector:

$$\text{for } v_1 : y = -\frac{1}{\tan\theta_1}x + \frac{v_1}{\cos\theta_1} \qquad [3]$$

$$\text{for } v_2 : y = -\frac{1}{\tan\theta_2}x + \frac{v_2}{\cos\theta_2} \qquad [4]$$

Each axial velocity component, $v_n$, is calibrated directly from the frequency shift $\Delta f_n$ along its respective color Doppler vector, as shown in the following equation:

$$v_n = \frac{\Delta f_n}{f} c \qquad [5]$$

In the above equation, c is the velocity of sound in the medium being insonated and $f$ is the frequency of the transmitted ultrasonic beam.

In one embodiment of the present invention, the two color Doppler vectors are steered at equal but opposite angles, $\theta_2$ and $-\theta_2$, with respect to a perpendicular from the face of the linear array transducer. Thus, the following angular relationships apply:

$$\theta_1 = \pi - \theta_2 \qquad [6]$$

$$\cos\theta_1 = -\cos\theta_2 \qquad [7]$$

$$\tan\theta_1 = -\tan\theta_2 \qquad [8]$$

Solving the simultaneous equations 3 and 4 for the endpoint coordinates (x, y) 414 of velocity vector $\bar{v}$, yields:

$$x = \frac{v_1 + v_2}{2} \frac{\sin\theta_2}{\cos^2\theta_2} \qquad [9]$$

$$y = \frac{v_2 - v_1}{2\cos\theta_2} \qquad [10]$$

From the computed values for x and y, the magnitude and direction of the velocity vector $\bar{v}$ can be computed using the following equations:

$$v = |\bar{v}| = \sqrt{x^2 + y^2} \qquad [11]$$

$$\phi = \tan^{-1}\frac{y}{x} \qquad [12]$$

Figure 6A:
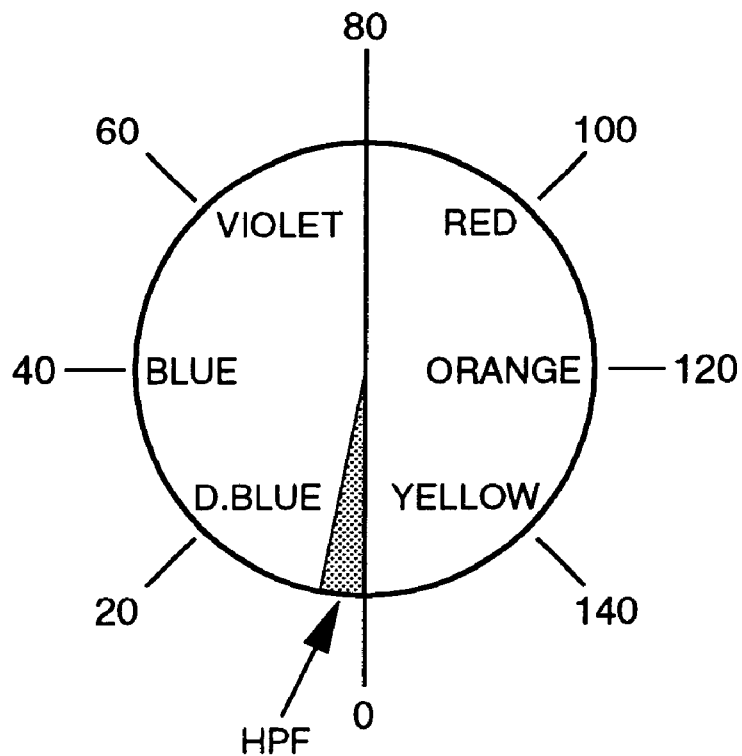
FIG. 6A illustrates a circular color scale in which absolute velocity of a vector is represented in color gradations, according to one embodiment of the present invention.

In one embodiment of the present invention, the resulting velocity vectors obtained at each angle are mapped onto a color scale in which dark hues represent low velocities and bright hues represent higher velocities. FIG. 6A illustrates a circular representation of a color scale in which the flow velocity is represented in color gradations, according to one embodiment of the present invention. In color wheel 600 for example, the range of color gradations are assigned velocity values from 0 to 160 cm/sec, with dark blue assigned a value of 20 cm/sec and yellow assigned a value of 140 cm/sec. It is to be noted that the velocity indicators on color wheel 600 are exemplary, and actual assigned velocity values will depend on the color Doppler pulse repetition frequency (PRF) and transmit frequency.

In the embodiment of the invention described above, it is assumed that the axial velocity components, $v_1$ and $v_2$, are determined in relation to the same velocity vector $\bar{v}$. This assumption necessitates that the Doppler vector pairs used to generate $v_1$ and $v_2$ are very nearly coincident in time such that $\bar{v}$ has not changed appreciably from the first Doppler vector, $v_1$, to the second Doppler vector, $v_2$. Therefore, this embodiment of the present invention requires that the color Doppler vectors be sequenced within 3–5 milliseconds or less of one another to ensure sample volume temporal coincidence.

Figure 7A:
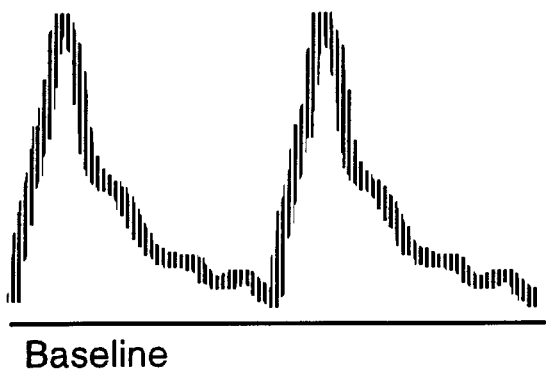
FIG. 7A illustrates exemplary arterial and venous blood flow waveforms for pulsality indices calculated over several cardiac cycles.
Figure 7A:
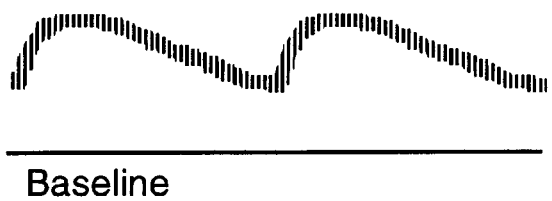

In an alternative embodiment of the invention, a pulsatility index (PI) can be computed over one or several cardiac cycles and used to differentiate between arterial and venous blood flows at each duplex color Doppler sample volume. Such a method is described in U.S. patent application Ser. No. 08/561,887, which is assigned to the assignee of the present application. FIG. 7A illustrates exemplary arterial and venous blood flow waveforms or pulsatility indices calculated over several cardiac cycles. In this alternative embodiment, a sequence of flow samples over time at each sample volume is taken to produce distinct venous peaks 700 and arterial peaks 702.

Figure 7B:
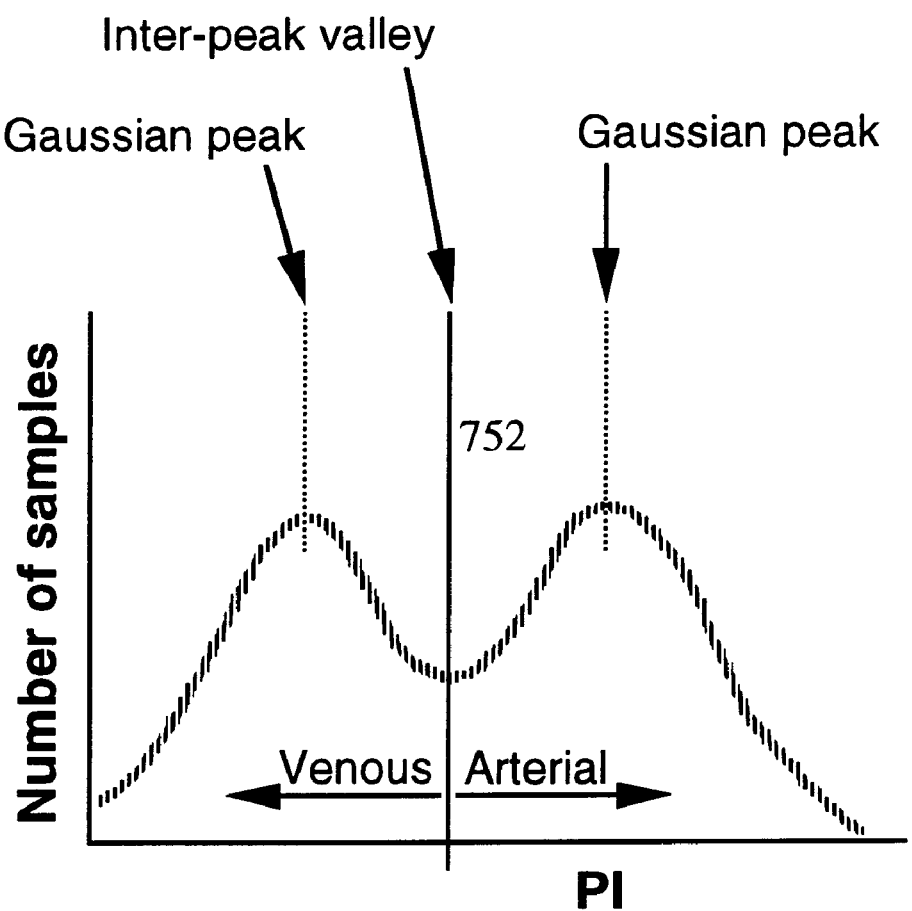
FIG. 7B illustrates exemplary venous and arterial peaks produced for a pulsality index computed over several cardiac cycles, according to an alternative embodiment of the present invention.

FIG. 7B illustrates an example of the venous and arterial peaks produced for a pulsatility index computed over several cardiac cycles according to an alternative embodiment of the present invention. In graph 750, the primary valley 752 between the peaks is taken as the dividing line between venous and arterial flows. All sample volumes with pulsatility indices below the dividing line are assigned colors in the venous color scale (e.g., blue-green), while all sample volumes with pulsatility indices above the dividing line are assigned colors in the arterial color scale (e.g., red-orange-yellow).

Figure 6B:
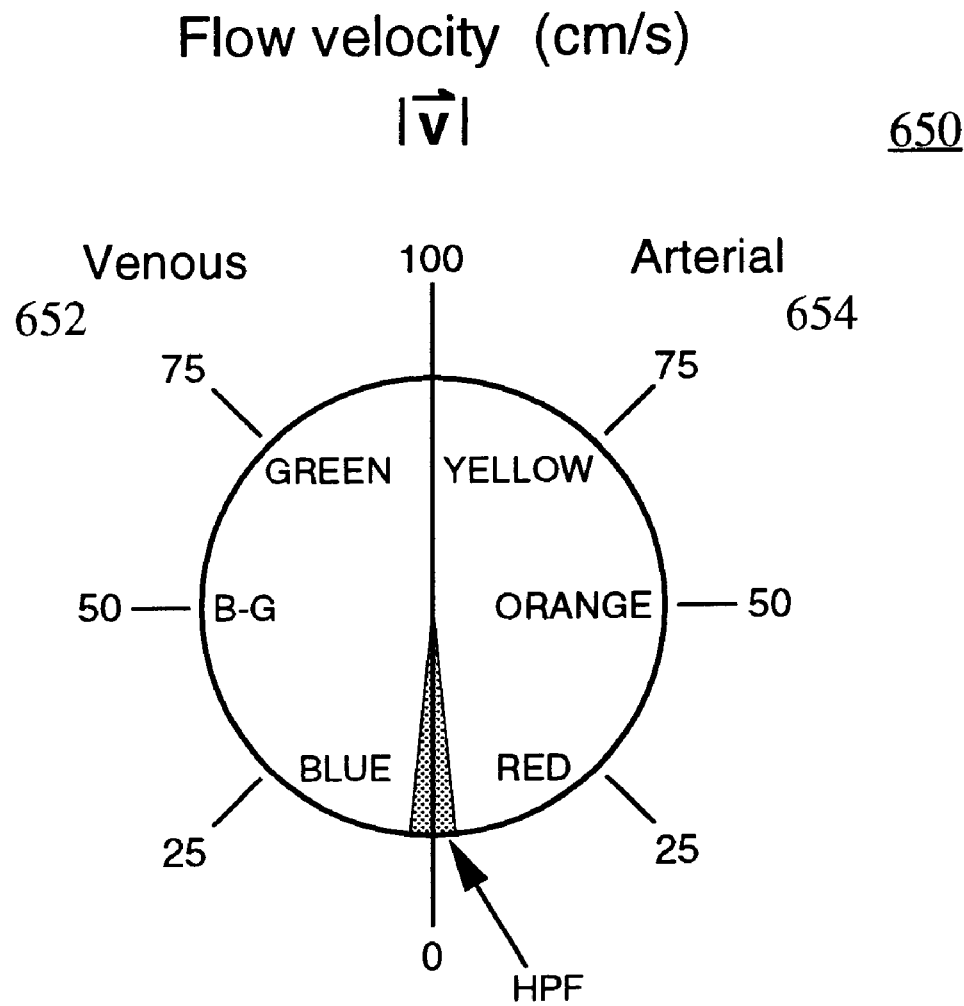
FIG. 6B illustrates a circular color scale in which absolute velocity of a vector is represented in color gradations, according to an alternative embodiment of the present invention.

FIG. 6B illustrates a circular representation of a color scale in which the flow velocity of the velocity vector is represented in color gradations, according to this alternative embodiment of the present invention. For color wheel 650, the range of color gradations for both the venous color scale 652 and the arterial color scale 654 are assigned values, for example, from 0 to 100 cm/sec. The venous color scale includes blue (value 25 cm/sec) to green (value 75 cm/sec), and the arterial color scale includes red (value 25 cm/sec) to yellow (value 75 cm/sec). Again, it is to be noted that the velocity indicators on color wheel 650 are exemplary, and actual assigned color values will depend on the color Doppler pulse repetition frequency (PRF) and transmit frequency.

Figure 8:
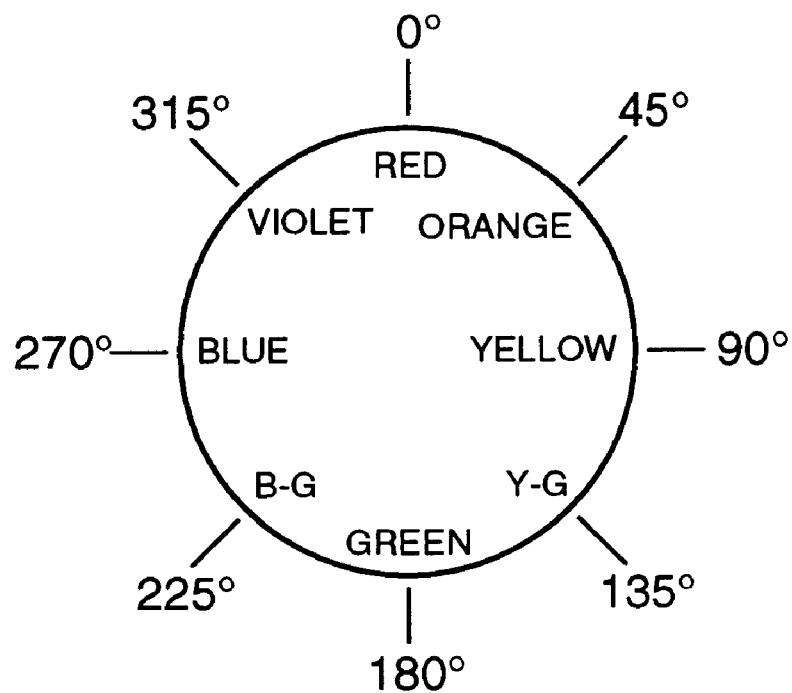
FIG. 8 illustrates a circular color scale in which the direction of a velocity vector is represented in color gradations, according to one embodiment of the present invention.

Besides the flow velocity, the direction of flow can also be mapped onto a circular color scale in which each color or hue around the scale is assigned to a particular direction of flow. FIG. 8 illustrates a circular color scale 800 in which flow or motion direction of a vector is represented in color gradations, according to one embodiment of the present invention. When flow pixels within the color Doppler velocity imaging (CDVI) region of interest are color mapped according to flow direction, a color Doppler direction image (CDDI) is obtained.

Color Doppler Velocity and Direction Imaging Device

In one embodiment of the present invention, a color Doppler velocity and direction imaging system includes elements of a conventional color Doppler ultrasound system in conjunction with steerable linear array transducers to compute and display absolute mean velocity and direction of fluid flow or tissue motion within a targeted region of interest.

Figure 9:
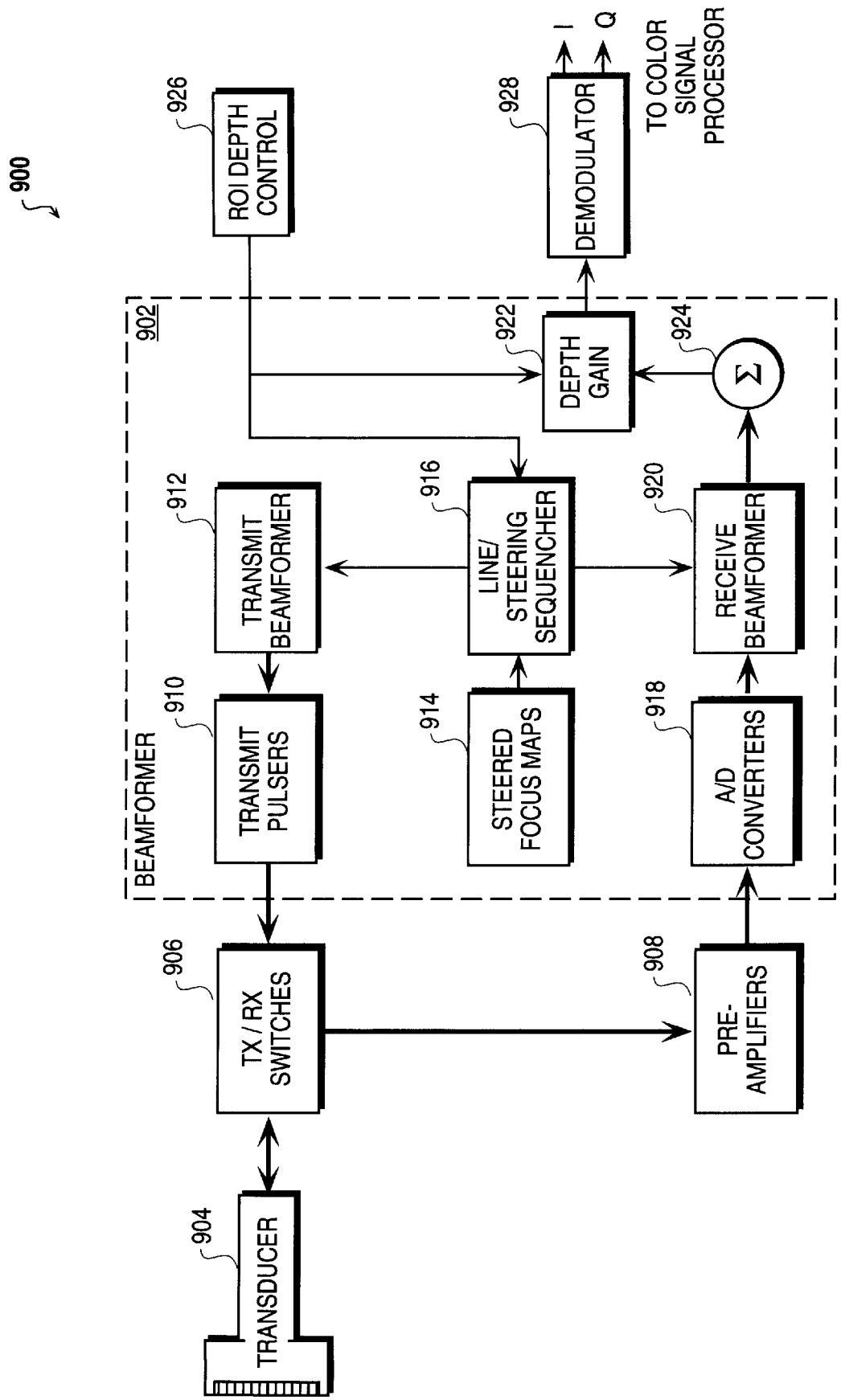
FIG. 9 is block diagram representation of a linear array transducer and beamformer circuit used in a color Doppler ultrasound system, according to one embodiment of the present invention.

FIG. 9 is a block diagram representation of a linear array transducer and beamformer circuit used in a color Doppler ultrasound system, according to one embodiment of the present invention. In system 900, linear array transducer 904 is coupled to beamformer circuit 902 through transmit/receive (Tx/Rx) switches 906 and preamplifier circuit 908. The linear array transducer 904 generates a sequence of angle-interleaved steered color Doppler vectors across the length of the color Doppler region of interest. In one embodiment of the present invention, the beams comprising a sequence are generated at less than 5 millisecond intervals to ensure that each Doppler vector pair used to generate the x and y components of the velocity vector are nearly coincident in time, as described above. In one embodiment of the present invention, beamformer circuit 902 is included in transmitter/receiver circuitry 102 in ultrasound system 100 illustrated in FIG. 1.

In the beamformer circuit 902, color Doppler ultrasound beams are sequenced to alternate between beam steering angles $\theta_2$ and $-\theta_2$ such that sequence beam pairs intersect at mid-depth within the color Doppler region of interest. This ensures that, on average, all coincident color Doppler sample volumes are as close to each other as possible in time. Region of interest (ROI) depth information is produced by ROI depth control circuit 926. Data from ROI depth control circuit 926 and steered focus maps 914 is input to line and steering sequencer 916. The line and steering sequencer 916 selects focus maps from steered focus maps circuit 914 for the appropriate range of depths and steering angles of the color Doppler ultrasound beams. Line and steering sequencer 916 then selects angle-interleaved steered color Doppler vectors for pairing. Line and steering sequencer 916 also selects additional unpaired vectors to define the beginning and end of the region of interest.

The paired and unpaired vectors are transmitted through transmit beamformer circuit 912 and transmit pulser circuit 910. The resulting ultrasound waveform sequences are then transmitted through switches 906 to transducer 904 for introduction into the tissue in the region of interest. The paired and unpaired vectors produced by sequencer 916 form the CDVI region of interest 310 illustrated in FIG. 3.

Returning ultrasound beams from the region of interest are picked up by transducer 904, routed through switches 906, amplified by pre-amplifier circuits 908 and converted from analog to digital signals in analog-to-digital (A/D) converter circuits 918. The received digital signals are then transmitted to receive beamformer circuit 920. The received sequences are summed in addition circuit 924, and the summed value of these sequences is combined with output from ROI depth control circuit 926 in depth gain circuit 922. The output from depth gain circuit 922 is input to demodulator 928 which produces in-phase (I) and quadrature (Q) signals that are input to a color signal processor.

Figure 10A:
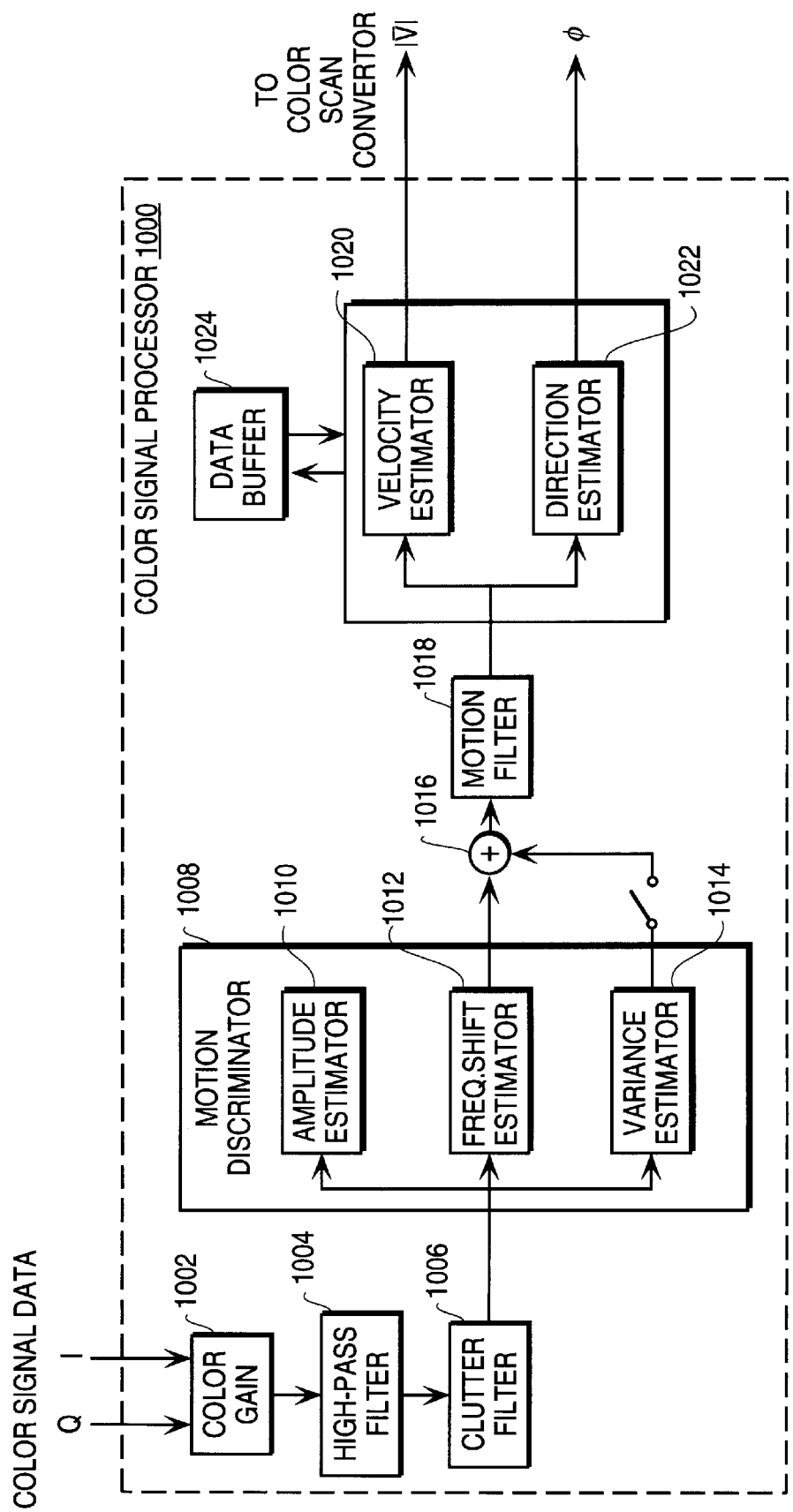
FIG. 10A is a block diagram of a color signal processing circuit within the color Doppler velocity and direction imaging system, according to one embodiment of the present invention.

FIG. 10A is a block diagram of a color signal processor circuit within the color Doppler velocity and direction imaging system according to one embodiment of the present invention. Color signal processor 1000 receives in-phase (I) and quadrature (Q) signals from demodulator 928 in FIG. 9. The in-phase and quadrature signals comprise the ultrasound signal data received from the ultrasound transducer. The I/Q signals are input to color gain circuit 1002. Output from gain circuit 1002 is input to a high pass filter 1004. The output signal from the high pass filter 1004 is input through a clutter filter 1006 to a motion discriminator circuit 1008.

Motion discriminator circuit 1008 includes separate units that extract different parameters of motion that may be exhibited differently in different types of tissue. Motion discriminator circuit 1008 includes amplitude estimator 1010, frequency-shift estimator 1012, and variance estimator 1014. Amplitude estimator 1010 extracts only the amplitude of the tissue motion based on the number of reflectors, while frequency-shift estimator 1012 extracts only the frequency shift component of the tissue motion. The variance estimator 1014 measures the spread of velocities of the tissue motion which provides information useful in discriminating among the different types of tissue present in the scanned region of interest.

The output from variance estimator 1014 is input through a switch to combinatorial circuit 1016. Combinatorial circuit 1016 combines this input with the output from frequency-shift estimator 1012 and processes these signals according to an operation provided by a programmable formula. In one embodiment of the present invention, the programmable formula used for combinatorial circuit 1016 is an addition operation to estimate the peak frequency shift.

The output from combinatorial circuit 1016 is input into a motion filter 1018. Motion filter 1018 removes flash motion artifacts, and serves to improve the signal-to-noise ratio of the system. The output from motion filter 1018 is input into a velocity estimator 1020 and a direction estimator 1022.

In one embodiment of the present invention, color Doppler signal processor 1000 uses conventional color Doppler algorithms to estimate mean frequency shifts, using frequency shift estimator 1012, between the transmitted and received ultrasound beams. The frequency-domain variance estimate, from variance estimator 1014, is then added to the mean frequency shift estimate to provide an estimate of peak frequency shift. The summed result is stored in a memory buffer 1024.

In one embodiment of the present invention, color Doppler ultrasound beams are sequenced between alternating beam steering angles $\theta_2$ and $-\theta_2$. Thus, results for the estimated mean frequency shifts are computed and stored for a first ultrasound beam at angle $\theta_2$, and then results for the estimated mean frequency shifts are computed for an oppositely steered ultrasound beam at angle $-\theta_2$. When data from coincident color Doppler sample volumes on the oppositely-steered color Doppler vectors is processed, the two frequency shifts are used in equations 9–12:

$$x = \frac{v_1 + v_2}{2} \frac{\sin\theta_2}{\cos^2\theta_2} \quad [9]$$

$$y = \frac{v_2 - v_1}{2\cos\theta_2} \quad [10]$$

$$v = |\vec{v}| = \sqrt{x^2 + y^2} \quad [11]$$

$$\phi = \tan^{-1}\frac{y}{x} \quad [12]$$

Solving the above equations provides estimates of the absolute velocity and direction of flow or motion within the duplex sample volume. In FIG. 10, the absolute velocity, v, is calculated in velocity estimator 1020, and the direction of flow, $\phi$, is calculated in direction estimator 1022.

In one embodiment of the present invention, the velocity and direction data are scan converted in a color scan converter, such as color scan converter 108 in FIG. 1. The scan converted data is then bilinearly interpolated into a two-dimensional matrix. The resulting flow pixel values are then mapped into a color scale for CDVI, such as shown in FIG. 6A, or CDDI, such as shown in FIG. 8. The mapped pixel values are then used to form an image for display on a display device, such as video display 130 in FIG. 1. For this embodiment, color signal processor 1000 is included within color flow processor 104 illustrated in FIG. 1.

Figure 10B:
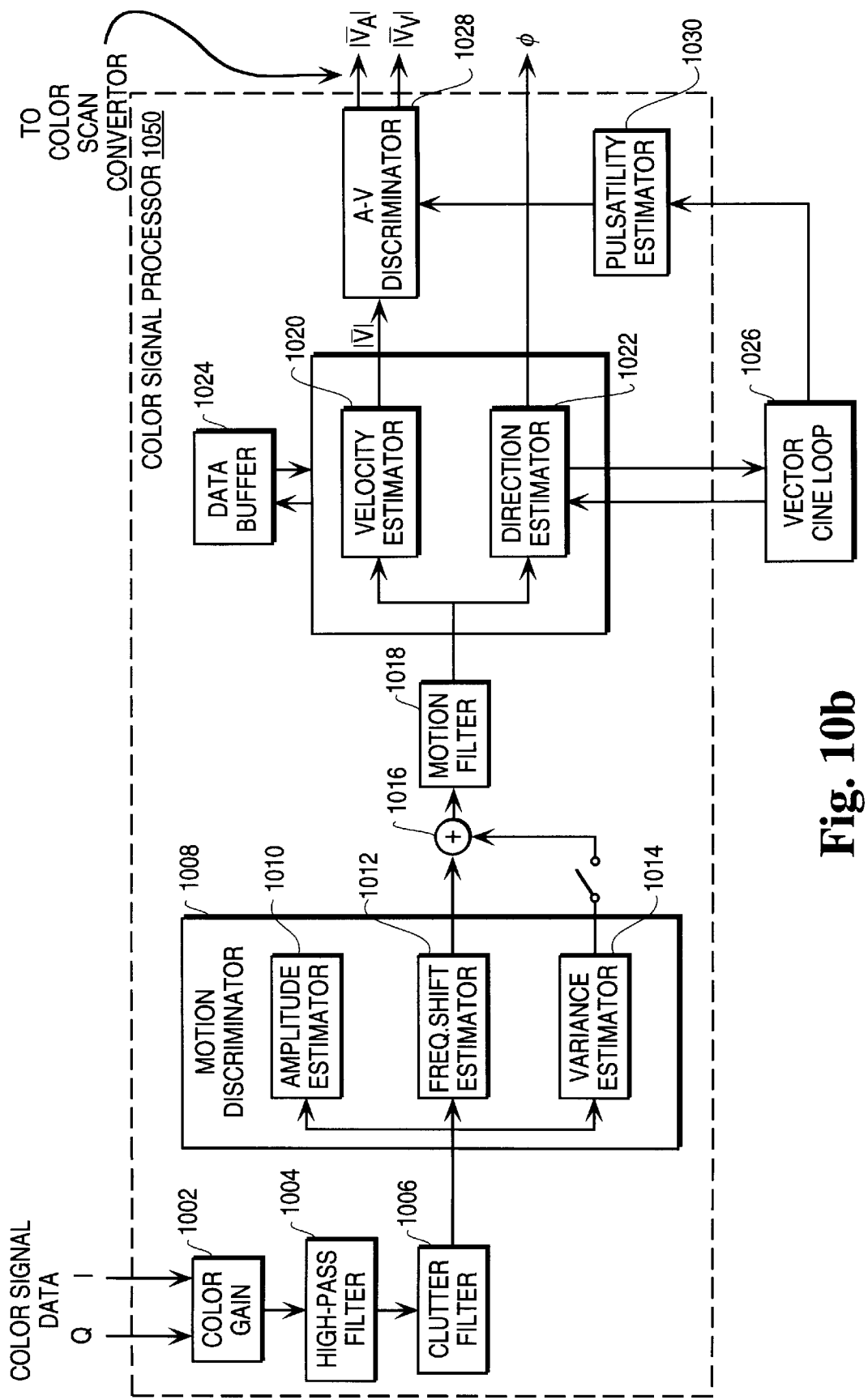
FIG. 10B is a block diagram of a color signal processing circuit within the color Doppler velocity and direction imaging system, according to an alternative embodiment of the present invention.

If the target area is a blood vessel or similar structure that contains flowing fluids, a pulsatility estimator can be used to determine a pulsatility index. FIG. 10B is a block diagram of a color signal processor circuit within the color Doppler velocity and direction imaging system according to an alternative embodiment of the present invention. In color signal processor 1050 of FIG. 10B, includes a pulsatility estimator 1030 that uses velocity data over one or more cardiac cycles is to compute the pulsatility index. The pulsatility index is then used by arterial-venous (A-V) discriminator 1028 to determine whether a flow is arterial or venous. In general, arterial flow is characterized by a relatively high pulsatility, and venous flow is characterized by a relatively low pulsatility. The velocity estimates are then categorized into arterial velocity $V_A$ or venous velocity $V_V$. The velocity estimates, together with the direction data, $\phi$, from direction estimator 1022 are then input to color scan converter 108 for generation of two-dimensional pixel data for display on video display 130.

In one embodiment of the present invention, a quantitative readout from any flow pixel in the color Doppler region of interest displays the estimated mean velocity, peak velocity, and angular direction of flow or motion. The desired color pixel may then be selected by an operator-controlled pointing device, such as a trackball or other similar cursor control device 126, as illustrated in FIG. 1. By selecting a particular pixel, an immediate readout of the estimated mean velocity, peak velocity, and direction of motion for the pixel may be obtained.

It should be noted that the precise arrangement and ordering of certain processes and circuits in the block diagrams of FIGS. 9 and 10 may vary with a number of possible beamformer and color signal processor designs, and that the present invention is not limited to the exact structures and embodiments illustrated.

Figure 11:
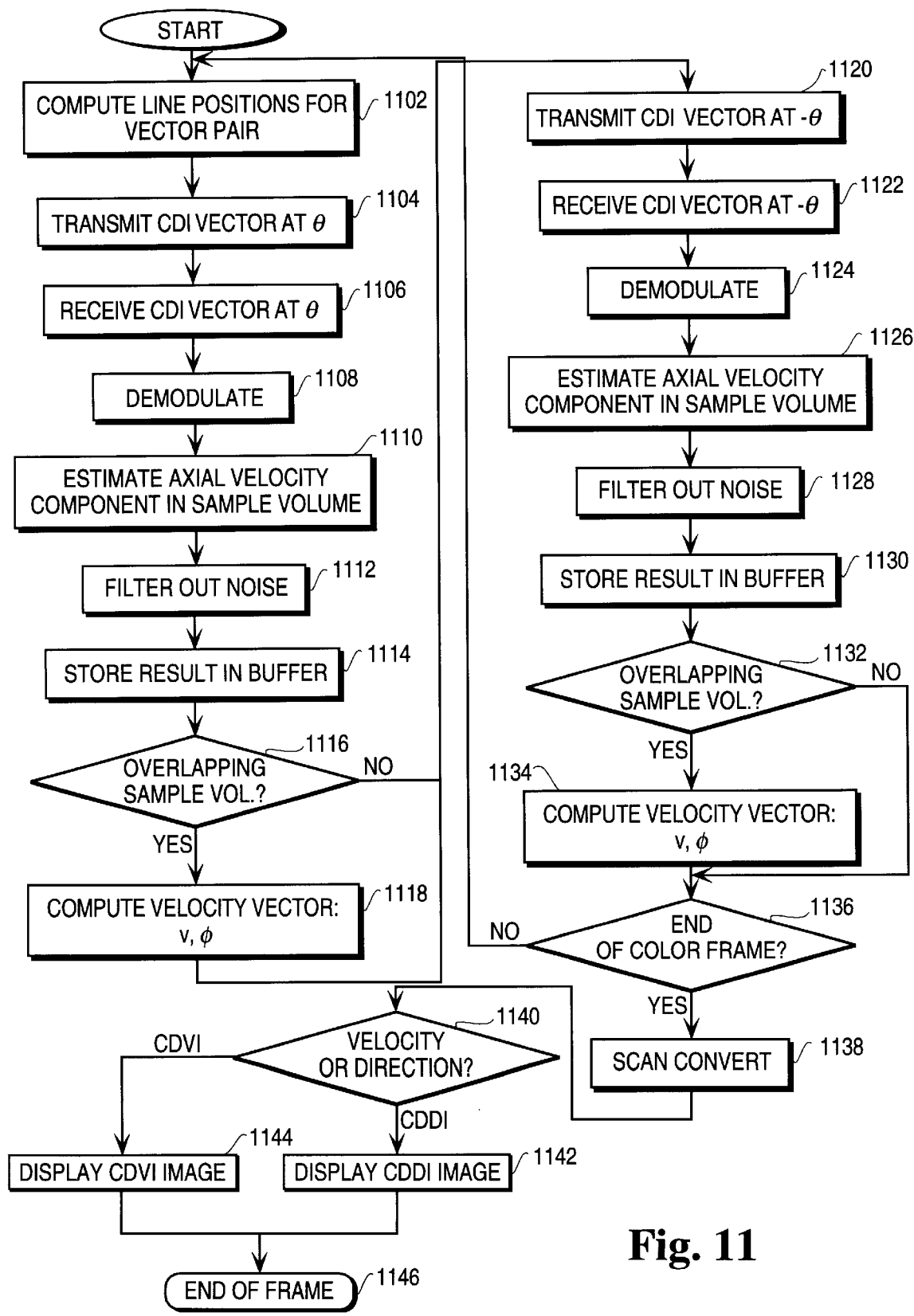
FIG. 11 is a flow chart illustrating the steps of performing color Doppler velocity and direction imaging according to a method of the present invention.

FIG. 11 is a flow chart illustrating the steps of performing color Doppler velocity and direction imaging according to a method of the present invention. The flow chart of FIG. 11 illustrates the processing sequence for alternating color Doppler beams steered at angles $\theta$ and $-\theta$. After each axial frequency shift estimate is obtained, if there is a previous coincident sample volume, v and $\phi$ are computed. For purposes of explanation, the steps of the method illustrated in FIG. 11 will be discussed in reference to FIGS. 9 and 10A, however elements of the method of FIG. 11 are not limited to these specific embodiments.

In step 1102, line positions for each vector pair are computed. The line positions for each vector pair are computed such that the sequence of beam pairs intersect at mid-depth within the region of interest. A first color Doppler image vector is transmitted by a linear array transducer at angle $\theta_2$, step 1104. In step 1106 the color Doppler image vector at angle $\theta_2$ is received by the linear array transducer. The received color Doppler image vector is then demodulated in a demodulator (e.g., demodulator 928 of FIG. 9), step 1108.

From the in-phase and quadrature signals produced from the demodulated color Doppler image vector, the axial velocity component in the sample volume of the region of interest is estimated, step 1110. In step 1112, noise from the estimated axial velocity component is filtered out, such as by using high-pass filter 1004 of FIG. 10. The resulting estimated axial velocity component is then stored in a memory buffer, step 1114. In step 1116, it is determined whether there is a previous coincident sample volume corresponding to the axial frequency shift estimate. If in step 1116 it is determined that there is a coincident (or overlapping) sample, the velocity vector is computed, step 1118, from the two overlapping samples. Computing the velocity vector comprises the steps of determining the magnitude of the velocity defined by $v_1$ and the direction of the velocity vector defined by the angle $\phi$.

In step 1120, a second color Doppler image vector is transmitted by the linear array transducer at angle $-\theta_2$. Note that, if in step 1116 it was determined that a previous sample volumes did not overlap, the process proceeds directly from step 1114 to step 1120 in which the Doppler image vector is transmitted at angle $-\theta_2$. In step 1122, the color Doppler image vector at angle $-\theta_2$ is received by the linear array transducer. The received color Doppler image vector is then demodulated in demodulator 928 of FIG. 9.

In step 1126, the axial velocity component in the sample volume is estimated. Noise components from the estimated axial velocity component are then filtered out, step 1128, and the result is stored in a memory buffer, step 1130. In step 1132, it is determined whether there is a previous coincident sample volume corresponding to the axial frequency shift estimate. If in step 1132 it is determined that there is an overlapping sample, the velocity vector is computed, step 1134, from the two overlapping samples. As with the first vector, computing the velocity vector for the second vector comprises the steps of determining the magnitude of the velocity defined by $v$ and the direction of the velocity vector defined by the angle $\phi$.

After the velocity vector has been computed, it is next determined whether the process has proceeded through the end of a color frame, step 1136. Note that if, in step 1132 it is determined that the sample volumes do not overlap, the process proceeds directly from step 1136 in which it is determined whether there is an end of a color frame. If in step 1136 it is determined that the color frame is not completed, the process repeats from step 1102 in which a next color Doppler image vector is transmitted at the first angle $\theta_2$.

If however, in step 1136 it is determined that the process has reached the end of a color frame, the velocity and direction data for all samples are scan converted, step 1138. It is next determined whether the scan converted data is velocity or direction information, step 1140. If, in step 1140 it is determined that the scan converted information is velocity data, the color Doppler velocity image (CDVI) is displayed, step 1144. If however, in step 1140 it is determined that the scan converted information is direction data then the color Doppler direction image (CDDI) is displayed, step 1142. The process for that particular color frame then ends, step 1146.

In the foregoing, a system has been described displaying the absolute velocity and direction of flow or tissue motion using ultrasonic color Doppler imaging. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. An ultrasonic imaging apparatus comprising:
    a transducer operable to transmit into a first area, a first set of ultrasound beams at a first angle and a second set of ultrasound beams at a second angle, and to receive from said first area, reflected ultrasound beams at said first angle and said second angle;
    a beamformer coupled to said transducer and operable to sequence a plurality of beams of said first set of ultrasound beams with a plurality of beams of said second set of ultrasound beams, such that successive ultrasound beams alternate between said first angle and said second angle; and
    a signal processor coupled to said beamformer and operable to estimate a first frequency shift of an object in said first area using an ultrasound beam of said first set of ultrasound beams, and to estimate a second frequency shift of said object using an ultrasound beam of said second set of ultrasound beams.

2. The ultrasonic imaging apparatus of claim 1 wherein said signal processor is further operable to compute an absolute velocity and direction of motion of said object using said first estimated frequency shift and said second estimated frequency shift.

3. The ultrasonic imaging apparatus of claim 2 further comprising a Doppler processor, and wherein said signal processor estimates said first frequency shift and said second frequency shift using one or more Doppler algorithms.

4. The ultrasonic imaging apparatus of claim 3 wherein said first angle and said second angle are equal and opposite angles with respect to a perpendicular line from a plane defined by a surface of said linear array transducer.

5. The ultrasonic imaging apparatus of claim 4 wherein a first vector is defined by an ultrasound beam at said first angle and a second vector is defined by an ultrasound beam at said second angle, said first vector and said second vector intersecting at said object, and wherein said first angle and said second angle are defined in relation to said first and second vector and an orthogonal axis, and further wherein said absolute velocity and said direction of motion are computed using trigonometric relationships between said first vector and said second vector and said orthogonal axis.

6. The ultrasonic imaging apparatus of claim 5 further comprising:
    a scan converter coupled to said signal processor and operable to convert said absolute velocity and direction into corresponding two-dimensional velocity data and two-dimensional direction data;
    a video processor coupled to said scan converter and operable to process said velocity data and said direction data into corresponding velocity pixel data and direction pixel data; and
    a video display device coupled to said video processor and operable to display said velocity pixel data and said direction pixel data.

7. The ultrasonic imaging apparatus of claim 6 wherein said scan converter comprises a color scan converter circuit, and wherein:
    said velocity data is mapped onto a first color scale, wherein different color values are assigned to different velocity magnitudes; and
    said direction data is mapped onto a second color scale, wherein different color values are assigned to different directions.

8. The ultrasonic imaging apparatus of claim 7 further comprising a motion discriminator circuit, said motion discriminator circuit comprising:

an amplitude estimator circuit configured to extract amplitude information from ultrasound Doppler image data for said object;

a velocity estimator circuit configured to extract frequency shift information from said ultrasound Doppler image data; and a variance estimator circuit configured to extract frequency shift distribution information from said ultrasound Doppler image data.

9. The ultrasonic imaging apparatus of claim 8 further comprising a combinatorial circuit coupled to said motion discriminator circuit, said combinatorial circuit operable to accept as input data, output values from said velocity estimator circuit and said variance estimator circuit, and to combine said input data in accordance with a formula programmed into said ultrasonic imaging apparatus.

10. The ultrasonic imaging apparatus of claim 5 further comprising:

a pulsatility estimator coupled to said motion discriminator circuit and operable to compute a pulsatility index for flow of fluid within said first area; and a discriminator circuit coupled to said pulsatility estimator and operable to differentiate between arterial blood flow and venous blood flow within said area.

11. The ultrasonic imaging apparatus of claim 7 wherein said pulsatility estimator circuit computes said pulsatility index using velocity data for said blood flow over one or more cardiac cycles of a patient examined by said ultrasonic imaging apparatus.

12. A method of performing ultrasonic imaging comprising the steps of:

(a) transmitting a first ultrasound beam at a first angle into a region of interest;

(b) transmitting a second ultrasound beam at a second angle into said region of interest;

(c) receiving a first reflected beam from said first ultrasound beam and a second reflected beam from said second ultrasound beam in a transducer, said first and second reflected beams reflected from acoustic reflectors in said region of interest;

(d) defining a first vector from said first reflected beam and a second vector from said second reflected beam; and (e) determining an absolute magnitude and direction for a velocity vector defined by motion of said acoustic reflectors in said region of interest using said first vector and said second vector.

13. The method of claim 12 wherein said first angle and said second angle are equal and opposite angles with respect to a perpendicular line from a plane defined by a surface of a transducer used to transmit said first ultrasonic beam and said second ultrasound beam.

14. The method of claim 13 further comprising the steps of (f) estimating a first frequency shift of said acoustic reflectors, wherein said first frequency shift is proportional to said first vector; and (g) estimating a second frequency shift of said acoustic reflectors, wherein said second frequency shift is proportional to said second vector.

15. The method of claim 14 wherein said step of estimating said first frequency shift and said step of estimating said second frequency shift comprise the step of using one or more Doppler algorithms.

16. The method of claim 15 further comprising the steps of:

(h) demodulating and isolating frequency shift and variance information from said received first reflected beam and said second reflected beam;

(i) computing Doppler imaging values from said frequency shift and variance information in accordance with a pre-determined relationship;

(j) scan converting said Doppler imaging values for complete frames into a raster format; and (k) assigning gray-scale or color values to said Doppler imaging values for display on a display device.

17. The method according to 15 further comprising the steps of:

(h) computing a pulsatility index using velocity data for motion of said acoustic reflectors in said region of interest over one or more cardiac cycles of an examined subject;

(i) discriminating between arterial flow and venous flow; and (j) assigning different gray-scale or color value ranges to said arterial flow and said venous flow for display on a display device.

18. A method of determining the absolute velocity and direction of fluid flow or motion of an object within a body, said method comprising the steps of:

transmitting a first ultrasonic color Doppler beam at a first angle into a region of interest containing said object;

transmitting a second ultrasonic color Doppler beam at a second angle into said region of interest, wherein said first angle and said second angle are equal and opposite angles with respect to a perpendicular line from a plane defined by a surface of a transducer transmitting said first and said second ultrasonic color doppler beams, and wherein said first beam and said second beam intersect at said object;

estimating a first frequency shift of said object from said first beam and a second frequency shift of said object from said second beam; and calculating a velocity and direction of said object using said estimated first frequency shift and said second frequency shift.

19. The method of claim 18 further comprising the steps of:

transmitting a first sequence of ultrasound beams at said first angle into said region of interest;

transmitting a second sequence of ultrasound beams at said second angle into said region of interest; and interleaving said first and said second sequences of ultrasound beams such that successive transmitted ultrasound beams are incident to said object at opposite angles.

20. The method of claim 19 further comprising the steps of:

determining a pulsatility index of said acoustic reflectors in said region of interest to determine a velocity and direction of fluid flow within said region of interest; and processing a number of flow samples as a function of said pulsatility index to differentiate between a first type of flow and a second type of flow within said region of interest.

21. An apparatus comprising: transducer means for transmitting into a first area, a first set of ultrasound beams at a first angle and a second set of ultrasound beams at a second angle, and for receiving from said first area, reflected ultrasound beams at said first angle and said second angle;

beamformer means coupled to said transducer means for sequencing a plurality of beams of said first set of ultrasound beams with a plurality of beams of said second set of ultrasound beams, such that successive ultrasound beams alternate between said first angle and said second angle; and signal processing means coupled to said beamformer means for estimating a first frequency shift of an object in said first area using an ultrasound beam of said first set of ultrasound beams, and for estimating a second frequency shift of said object using an ultrasound beam of said second set of ultrasound beams.

22. The apparatus of claim 21 further comprising means for computing an absolute velocity and direction of motion of said object using said first estimated frequency shift and said second estimated frequency shift.

23. The apparatus of claim 22 further comprising Doppler processing means for processing said first estimated frequency shift and said second estimated frequency shift.

24. The apparatus of claim 23 further comprising video processing means for generating display data comprising gray-scale or color pixel data corresponding to velocity and direction of said object in said first area.

25. The apparatus of claim 21 further comprising:

variance estimating means for measuring spread of velocities of tissue motion in said first area to produce a frequency-domain variance estimate; and means for computing a peak velocity estimate of said object by adding said frequency-domain variance estimate to said first estimated frequency shift and to said second estimated frequency shift.

26. The apparatus of claim 25 further comprising video processing means for generating display data comprising gray-scale or color pixel data corresponding to peak velocity and direction of said object in said first area.

\* \* \* \* \*